United States Patent [19]

Beach

[11] Patent Number: 5,810,854
[45] Date of Patent: Sep. 22, 1998

[54] METHOD AND APPARATUS FOR ATTACHING CONNECTIVE TISSUE TO EACH OTHER OR UNDERLYING BONE

[76] Inventor: William R. Beach, 12465 Grace Hill La., Richmond, Va. 23060

[21] Appl. No.: 788,363

[22] Filed: Jan. 24, 1997

[51] Int. Cl.⁶ .................................................. A61B 17/04
[52] U.S. Cl. ...................... 606/151; 606/232; 24/16 PB; 24/17 AP
[58] Field of Search ..................... 606/151, 232; 24/16 PB, 17 AP, 30.5 P, 30.5 R

[56] References Cited

U.S. PATENT DOCUMENTS

| | | | |
|---|---|---|---|
| Re. 31,541 | 3/1984 | Wood | 24/16 PB |
| D. 224,960 | 10/1972 | Wilson | D9/252 |
| 1,380,472 | 6/1921 | Glisson . | |
| 2,935,773 | 5/1960 | Weckesser | 24/17 |
| 2,936,980 | 5/1960 | Rapata | 248/74 |
| 2,969,216 | 1/1961 | Hallsey | 248/71 |
| 2,979,794 | 4/1961 | Bartolo | 24/17 |
| 3,009,220 | 11/1961 | Fein | 24/16 |
| 3,049,771 | 8/1962 | Litwin et al. | 24/16 |
| 3,102,311 | 9/1963 | Martin et al. | 24/16 |
| 3,112,496 | 12/1963 | Dritz | 2/322 |
| 3,118,200 | 1/1964 | Bell | 24/16 |
| 3,146,012 | 8/1964 | King | 292/320 |
| 3,149,808 | 9/1964 | Weckesser | 248/74 |
| 3,197,829 | 8/1965 | Caveney et al. | 24/16 |

(List continued on next page.)

OTHER PUBLICATIONS

Joseph Iannotti, Jn Am Acad Orthop Surg., Vol. 2, No. 2, "Full–Thickness Rotator Cuff Tears: Factors Affecting Surgical Outcomes," Mar./Apr. 1994, pp. 87–95.

Primary Examiner—Gary Jackson
Attorney, Agent, or Firm—Roberts & Brownell, LLC

[57] ABSTRACT

A method and apparatus for attaching connective tissue to each other or to underlying bone is described. The invention includes a band with latching grooves to engage a detached clamping head. At one end of the band is an opening through which the other end of the band may pass to allow the band to form a loop. The end of the band is then inserted into the detached clamping head which has a ratcheting pawl which engages the grooves in the band to hold the band and prevent its slipping. The band may also have a bulb element at or near the end of the band with the opening. There may also be a number of disk or bulb elements to distribute the force on the tissue. The band may also have varying width to provide different force on the tissues. The band and clamping head may be manufactured of biocompatible polymers such as implantation grade nylon, polyethylene or biosoluble material. A method for use of the present invention to repair a torn rotator cuff is also described.

17 Claims, 6 Drawing Sheets

OTHER PUBLICATIONS

| Patent No. | Date | Inventor | Class |
|---|---|---|---|
| 3,224,056 | 12/1965 | Joffe | 24/16 |
| 3,368,247 | 2/1968 | Orban | 24/16 |
| 3,570,497 | 3/1971 | Lemole | 128/335.5 |
| 4,079,485 | 3/1978 | Collier et al. | 24/16 PB |
| 4,137,606 | 2/1979 | Wood | 24/16 PB |
| 4,201,215 | 5/1980 | Crossett | 128/335 |
| 4,263,697 | 4/1981 | Speedie | 24/30.5 P |
| 4,279,248 | 7/1981 | Gabbay | 128/92 EA |
| 4,287,644 | 9/1981 | Durand | 24/16 PB |
| 4,413,380 | 11/1983 | Suzuki | 24/16 PB |
| 4,458,385 | 7/1984 | Espinoza | 24/16 PB |
| 4,470,173 | 9/1984 | Adamson | 24/30.5 P |
| 4,501,049 | 2/1985 | Adamson | 24/30.5 P |
| 4,502,187 | 3/1985 | Kitagawa | 24/16 PB |
| 4,506,415 | 3/1985 | Swift | 24/16 PB |
| 4,516,293 | 5/1985 | Beran | 24/16 PB |
| 4,573,242 | 3/1986 | Lankton et al. | 24/16 PB |
| 4,574,434 | 3/1986 | Shupe et al. | 24/16 PB |
| 4,580,319 | 4/1986 | Paradis | 24/16 PB |
| 4,615,185 | 10/1986 | Bollinger | 63/5 R |
| 4,631,782 | 12/1986 | Gecs | 24/16 PB |
| 4,658,478 | 4/1987 | Paradis | 24/16 PB |
| 4,680,834 | 7/1987 | Andre et al. | 24/16 PB |
| 4,730,615 | 3/1988 | Sutherland | 128/335 |
| 4,735,387 | 4/1988 | Hirano et al. | 248/71 |
| 4,776,067 | 10/1988 | Sorensen | 24/16 PB |
| 4,788,751 | 12/1988 | Shely et al. | 24/16 PB |
| 4,813,416 | 3/1989 | Pollak et al. | 128/335 |
| 4,862,560 | 9/1989 | Lichtenberg | 24/16 PB |
| 4,866,816 | 9/1989 | Caveney | 24/16 PB |
| 4,882,813 | 11/1989 | Nakamura | 24/16 PB |
| 4,944,475 | 7/1990 | Ono et al. | 248/71 |
| 4,950,284 | 8/1990 | Green et al. | 606/216 |
| 4,950,285 | 8/1990 | Wilk | 606/232 |
| 4,958,414 | 9/1990 | Benoit | 24/16 PB |
| 4,988,355 | 1/1991 | Leveen et al. | 606/158 |
| 5,042,114 | 8/1991 | Parrish | 24/16 PB |
| 5,089,008 | 2/1992 | Chen | 606/216 |
| 5,123,913 | 6/1992 | Wilk et al. | 606/232 |
| 5,146,654 | 9/1992 | Caveney et al. | 24/16 PB |
| 5,193,250 | 3/1993 | Caveney | 24/16 PB |
| 5,207,694 | 5/1993 | Broome' | 606/148 |
| 5,224,244 | 7/1993 | Ikeda et al. | 24/16 PB |
| 5,230,541 | 7/1993 | Nowak | 292/288 |
| 5,269,809 | 12/1993 | Hayhurst et al. | 606/232 |
| 5,304,188 | 4/1994 | Marogil | 606/157 |
| 5,317,787 | 6/1994 | Fortsch | 24/16 PB |
| 5,356,412 | 10/1994 | Golds et al. | 606/74 |
| 5,363,536 | 11/1994 | Kleemann | 24/30.5 P |
| 5,366,461 | 11/1994 | Blasnik | 606/151 |
| 5,383,882 | 1/1995 | Buess et al. | 606/157 |
| 5,398,383 | 3/1995 | Bingold | 24/16 PB |
| 5,454,392 | 10/1995 | Trueb et al. | 137/375 |
| 5,456,246 | 10/1995 | Schmieding et al. | 600/201 |
| 5,459,907 | 10/1995 | Nivet | 24/484 |
| B1 5,317,787 | 11/1995 | Fortsch | 24/16 PB |

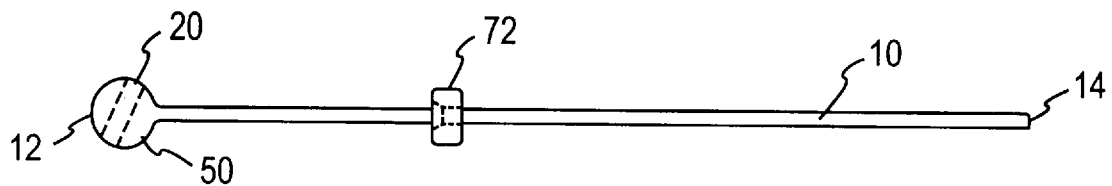
FIG. 4A
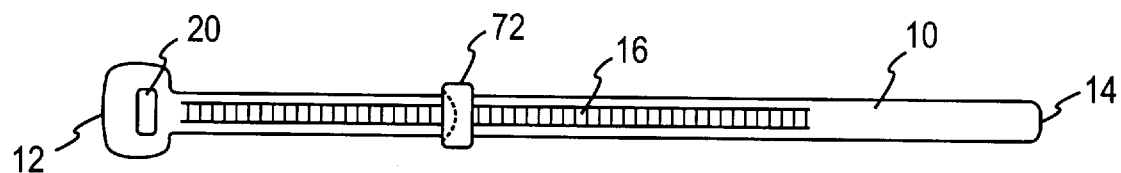
FIG. 4B
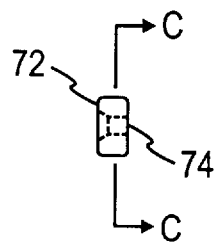 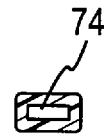
FIG. 4C  FIG. 4D

_5,810,854_

METHOD AND APPARATUS FOR ATTACHING CONNECTIVE TISSUE TO EACH OTHER OR UNDERLYING BONE

FIELD OF THE INVENTION

This invention relates generally to a device and method for holding torn or damaged ligament(s) or tendon(s) in close contact with each other or in close contact with the underlying bone to facilitate the reattachment process through normal healing, and more specifically to a device that can be easily applied, holds the soft connective tissues in the desired positions and causes minimal damage or injury to the tissues during the healing process.

DESCRIPTION OF RELATED ART

In the field of orthopaedic surgery, joint and muscle connective tissues (ligaments and tendons) must be reattached after they are torn or detached. The reattachments of those torn connective tissues to either other connective tissues or to the underlying bone are difficult. The torn tissues must remain in close contact throughout the healing process, which normally requires four to six weeks. If the tissues move significantly before becoming reattached, the healing process may never occur, resulting in an unstable joint or reduced range of motion because of the unattached tendon or ligament. When torn connective tissue is reattached to underlying bone, the problem is particularly difficult. This is partially because the structure of bone and connective tissue are very dissimilar and fastening methods that are appropriate for one, are less than appropriate for the other. The need to keep the tissues in close contact during healing is especially problematic for bone/connective tissue healing because the healing times of connective tissues are much longer than experienced in skin or other organs.

The physical realignment and stabilization of connective tissue and bone for reattachment is the most difficult part. Bone to bone connections use fasteners like screws and glues. Both glues and screws provide a solid attachment to the bone, resist movement and provide stability during the healing process. However, glues and screws are inadequate for attachment of connective tissues to the bone. None of the glues that are appropriate for bone are able to bond and hold connective tissues and enable natural healing. Screws further injure and weaken the connective tissue in the region of the tear, and because of their sizes, are only appropriate for repairs of large connective tissue tears on large bone structures. Screws also concentrate their force in a very small area and provide very little stability over the rest of the connective tissue. Additionally, screws may tear out of the connective tissue during joint movement.

Surgical sutures using silk or a variety of materials are generally used to hold connective tissues together during reattachment of connective tissue to other connective tissues. The suture does provide a flexible means of holding the connective tissues together, but the surface area of the suture itself is very limited and therefore the pressure per unit area on the connective tissue is very high which does not promote efficient healing. For attachment of connective tissue to underlying bone, sutures are wholly inadequate. The sutures must pierce the bone usually requiring wire rather than silk or other flexible materials.

Currently, it is very difficult to secure soft tissue to bone and to maintain close apposition. The sutures that are often used can elongate and lose this close apposition of soft tissue to bone. In addition, the physical act of tying the sutures is difficult because of trying to maintain apposition against counteracting tendon/ligament tension.

An example to illustrate the difficulty of attaching connective tissue to bone involves repair of anterior dislocations of the shoulder. As a result of shoulder dislocation, which occurs in two to eight percent of the population, the anterior/inferior glenohumeral ligament can be torn off the glenoid. In a majority of patients without additional treatment, the anterior/inferior glenohumeral ligament heals in a lax position allowing the shoulder to dislocate. In one form of treatment, this ligament can be re-tensioned by creating a cleavage plane between the labrum and the anterior/inferior glenohumeral ligament, thereby creating a raw surface for reattachment by abrading the anterior glenoid neck with a bur, drilling a pin through the glenoid, placing sutures in the anterior/inferior glenohumeral ligament and tying or tightening the sutures over the back of the scapula. This treatment encompasses all the difficulties of attaching connective tissue to bone.

Various rachet type clamping devices have been disclosed for surgical use. U.S. Pat. No. 5,304,188, issued to Marogil, discloses a removable surgical clamp device and method in the form of a plastic strap with ratchet type gripping mechanism which is passed around a solid organ to clamp off the desired portion and prevent or greatly reduce bleeding. The device of Marogil is a temporary device intended to reduce bleeding of solid organs during surgery and is removed before closing the incision. Marogil makes specific reference to removal of the surgical clamp device at the end of surgery, rather than leaving it in place. Marogil does not disclose a means for holding connective tissue to bone or other connective tissue for the purpose of positioning the tissues or stabilizing them in position.

Rachet type clamping devices are disclosed in U.S. Pat. No. 4,730,615 issued to Sutherland et al. and U.S. Pat. No. 4,813,416 issued to Pollak et al. Both patents disclose devices with bands to distribute the clamping force and a rachet device on one end for the purpose of holding the sternum together as typically follows open heart surgery. Both the Sutherland and Pollak patents contain features that are optimally designed for application to the sternum. Sutherland and Pollak do not disclose a means for holding connective tissue to bone or other connective tissue.

There are additional clamping devices for the purpose of holding the sternum together as typically follows open heart surgery. They include U.S. Pat. Nos. 4,279,248 issued to Gabbay; 4,201,215 issued to Crossett et al.; 5,356,412 issued to Golds et al.; and 5,366,461 issued to Balsnik. All these devices and methods are optimally designed for holding the sternum together. Gabbay, Crossett, Golds et al., and Balsnik do not disclose a means for holding connective tissue to bone or other connective tissue.

U.S. Pat. No. 3,570,497 issued to Lemole discloses a suture with needle end attached to a rachet type device that allows tissue closure much more quickly than can be done by conventionally tying a suture knot. Lemole is directed to reducing the time for application of sutures to soft tissue and/or dermic layer at the end of a surgical procedure. Lemole does not disclose a means for holding connective tissue to bone.

There are additional suture type devices with rachet type closures. They include U.S. Pat. Nos. 5,207,694 issued to Broome'; 5,123,913 issued to Wilk et al., 4,950,285 issued to Wilk; and 4,950,284 issued to Green et al. Each of these devices is directed toward use with soft tissues. Broome' discloses a means for performing a surgical occlusion which is applicable to laparotomy and laparoscopy. Wilk and Wilk et al. disclose a suture device which may be used in suturing operations as well as ligation of blood vessels and other ducts. Green et al. discloses a fascia clip used to provide a rapid closure of the fascia; that is, the fibrous tissue that envelopes the body beneath the skin. Broome, Wilk et al., Wilk, and Green et al. do not disclose a means for holding connective tissue to bone.

U.S. Pat. No. 5,456,246 issued to Schmieding et al. discloses a device for retracting the infrapatellar fat pad during arthroscopic knee surgery. Schmieding et al. does not disclose a means for holding connective tissue to bone or other connective tissue.

U.S. Pat. No. 05,383,882 issued to Buess et al. discloses a ligature device and an endoscopic instrument for application of the device. The ligature disclosed is a rachet type clamping device that is particularly appropriate for use with the endoscopic instrument. The device of Buess is optimally designed for endoscopic application with examples for use on abdominal organs. The shape and size of the rachet type clamping device disclosed in Buess is optimized for this use. Buess does not disclose a means for holding connective tissue to bone or other connective tissue.

A need exists for an easily applied device and method to hold connective tissues in close contact with each other or underlying bone during the healing process, while preventing further damage to the connective tissues.

SUMMARY OF THE INVENTION

It is therefore an objective of the present invention to provide a device and method for attaching torn or detached tendons and or ligaments to each other or to underlying bone to facilitate the natural healing process.

It is a further object of the present invention to provide this device and method using a rachet type clamping device that has a band with integral asymmetric teeth to achieve good holding power and a detached clamping head with ratchet type pawls to engage the integral teeth on the band.

It is a further object of the present invention to provide this device and method with one or multiple bulb or disk elements to dissipate or spread the clamping force on the clamped tissue.

It is a further object of the present invention to provide this device and method with an opening on the band to allow the surgeon to cinch the band and test the positioning of the tendon or ligament before attaching the detached clamping head.

It is a further object of the present invention to provide this device and method with provision for a bone anchor on the detached head to provide greater stability of the device in relation to the underlying bone.

It is a further object of the present invention to provide this device and method with provisions for varying the width of the band to dissipate or spread the clamping force on the clamped tissue.

It is a further object of the present invention to provide this device and method with provisions for varying the width of the band to concentrate the force per unit area on the connective tissue.

It is a further object of the present invention to manufacture this device from biocompatable polymers such as implantable grade nylon, polyethylene, or biosoluble material.

These and other objectives of the present invention will become obvious to those skilled in the art upon review of the following disclosure.

BRIEF DESCRIPTION OF THE DRAWINGS

FIG. 5: Illustrates an alternative embodiment of the band with a bulb in proximity to the head.

FIGS. 4A through 4D: Illustrates.

FIG. 4A: Illustrates an alternative embodiment of the band viewed from the side of the band.

FIG. 4B: Illustrates an alternative embodiment of the band viewed from the top of the band.

FIG. 4C: Illustrates a bulb and disk of an alternative embodiment of the present invention.

FIG. 4D: Illustrates a bulb of an alternative embodiment of the present invention viewed from the side of the bulb on the cut line C—C of FIG. 7C.

DETAILED DESCRIPTION

Figure 1A:
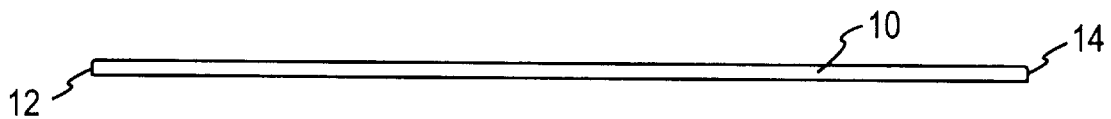
FIG. 1A: Illustrates a sideview of the band.
Figure 1B:
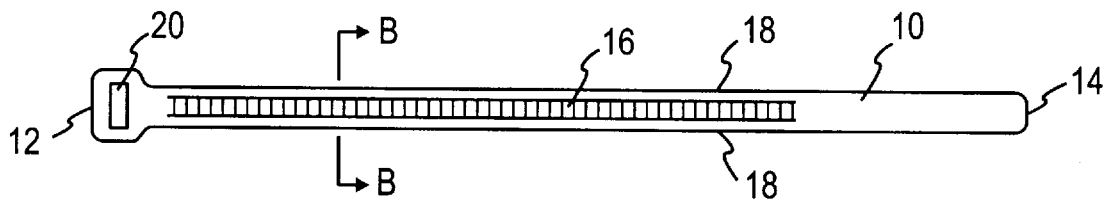
FIG. 1B: Illustrates a top view of the band.
Figure 1C:
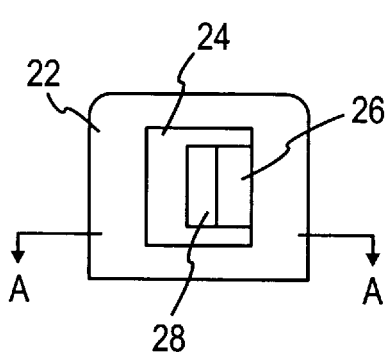
FIG. 1C: Illustrates a top view of the detached clamping head.
Figure 1D:
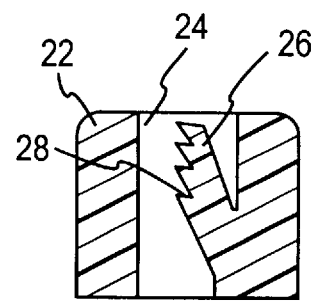
FIG. 1D: Illustrates the detached clamping head viewed from the side of the head on the cut line A—A of FIG. 1C.
Figure 1E:
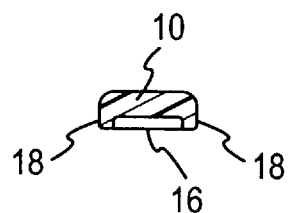
FIG. 1E: Illustrates the band viewed from the end of the band on the cut line B—B of FIG. 1B.

FIGS. 1A through 1E shows the preferred embodiment of the present invention. Referring to FIGS. 1A through 1E, the device of the present invention has band 10 with first end 12, second end 14, and multiple asymmetric teeth forming plurality of parallel locking grooves 16 that are recessed within sides 18 of band 10. In an alternative embodiment a, plurality of parallel locking grooves 16 is not recessed. At first end 12 of band 10 there is opening 20 through which second end 14 of band 10 may pass, thereby forming a loop. When band 10 is in this looped arrangement, detached clamping head 22 which has coupling hole 24 can be passed over second end 14 of band 10. Within clamping head 22 is locking member 26 having at least one ratchet pawl 28 that engages the plurality of locking grooves 16 on band 10. Ratchet pawl 28 extends obliquely from the inside wall of coupling hole 24 so as to retain band 10, and plurality of parallel locking grooves 16, within coupling hole 24. Because of this engagement, band 10 is slidable in only one direction. In the closed position, band 10 forms a loop and securely binds the tendons and ligaments to the collar or shoulder bones.

Figure 2:
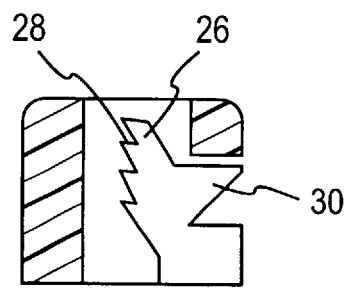

FIG. 2 shows an alternative embodiment of the present invention wherein the band may be disengaged by releasing the engagement between ratchet pawl 28 and the plurality of parallel locking grooves. This is accomplished by pushing downward end 30 of locking member 26 28 so that ratchet pawl 28 member 26 no longer communicate with the plurality of parallel locking grooves 16.

Figure 3A:
FIG. 3A: Illustrates an alternative embodiment of the detached clamping head viewed from the side of the head on the cut line A—A of FIG. 1C.
Figure 3B:
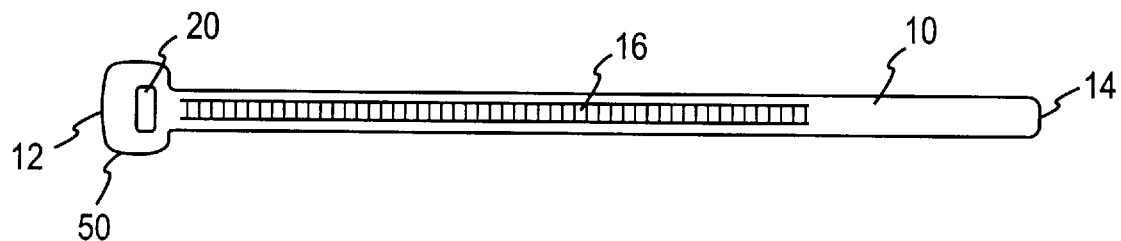
FIG. 3B illustrates an alternative embodiment (top view) of the band with a bulb in proximity to the head.

FIGS. 3A AND 3B shows an alternative embodiment of the present invention wherein first end 12 of band 10 has bulb element 50 which includes opening 20 and provides for a different apposition point. The surgeon can concentrate the force on a certain area of connective tissue through the accurate placement of bulb element 50.

FIG. 4A throygh 4D shows an alternative embodiment of the present invention wherein a plurality of disk elements are slidably attached to the band. Referring to FIGS. 4A and 4B, from one to a plurality of disk element(s) 72 may be slidably placed on band 10. Disk element(s) 72 are stopped by bulb element 50. Referring to FIGS. 4C and 4D, each disk element(s) 72 has attachment opening 74. Attachment opening 74 is of a size to allow band 10 to pass through disk element(s) 74, but the clearance between attachment opening 74 and band 10 is such that disk element(s) 74 does not easily slide along band 10. This close fit allows disk elements to be placed in an approximate position on the band and remain in that position before the band is cinched.

Figure 5A:
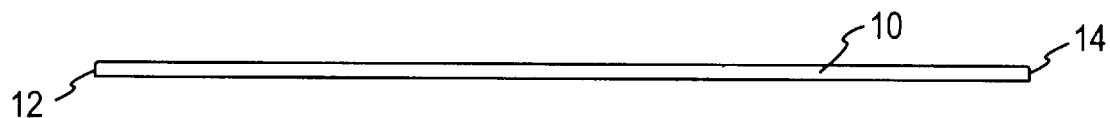
FIG. 5A Illustrates a side view of an alternative embodiment of the band.
Figure 5B:
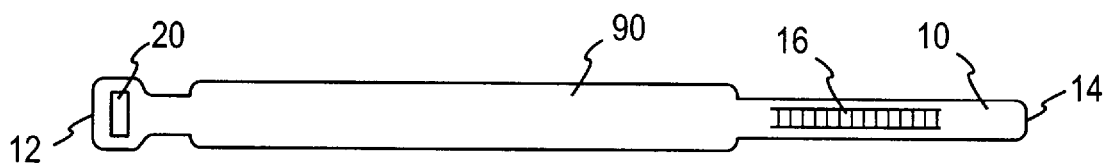
FIG. 5B: Illustrates a top view of an alternative embodiment of the band, wherein the band is wide.
Figure 5C:
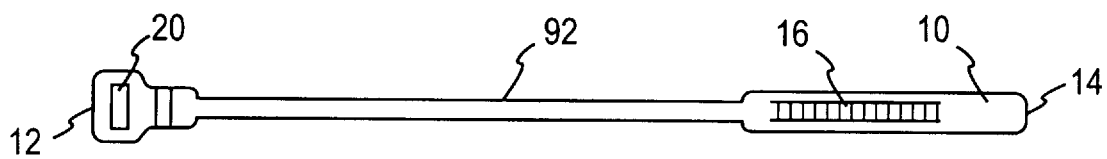
FIG. 5C: Illustrates a top view of an alternative embodiment of the band, wherein the band is narrow.

FIGS. 5A through 5C show an alternative embodiment of the present invention wherein the band has varying widths. Referring to FIG. 5B, band 10, has wider contact section 90, to distribute the force per unit area on the connective tissue. Referring to FIG. 5C, band 10, has narrower contact section 92, to concentrate the force per unit area on the connective tissue. These different shapes allow the surgeon to select a shape that is appropriate for the type of connection that is required.

Figure 6A:
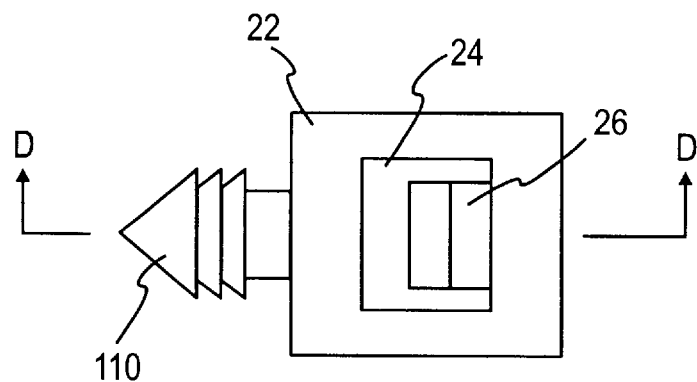
FIG. 6A: Illustrates an alternative embodiment of the clamping head viewed from the top of the head.
Figure 6B:
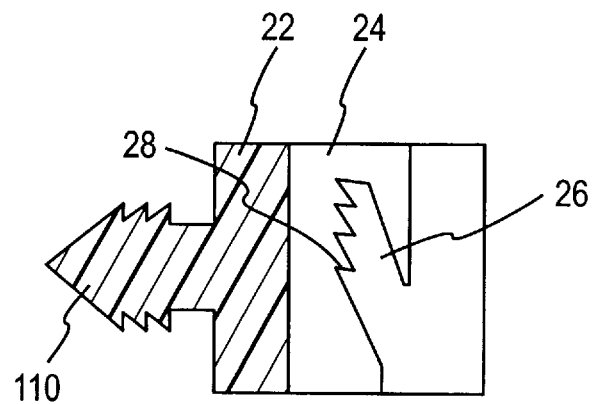
FIG. 6B: Illustrates an alternative embodiment of the clamping head viewed from the side of the head on the cut line D—D of FIG. 6A.

FIGS 6A and 6B show an alternative embodiment of the present invention wherein the clamping head has a bone anchor. Referring to FIGS. 6A and 6B, detached clamping head 22 has bone anchor 110, which is placed to allow coupling hole 24 to run parallel to the underlying bone. By creating a trough or hole in the bone and placing the bone anchor in the trough or hole, this gives the surgeon another alternative for anchoring soft tissue to bone.

Figure 7:
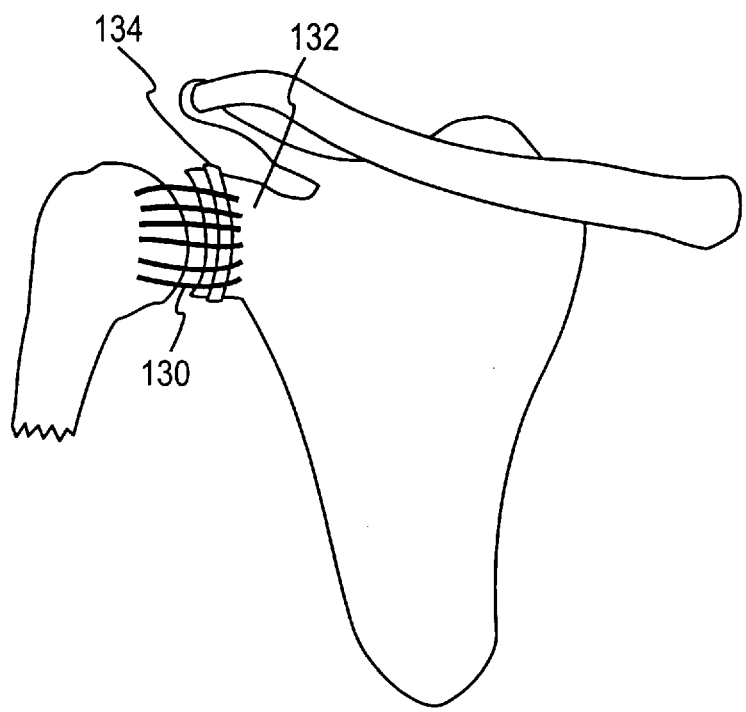
FIG. 7: Illustrates the use of the present invention in attaching a torn anterior/inferior glenohumeral ligament to the glenoid/glenoid neck.

FIG. 7 shows the placement and use of the present invention for reattachment of a torn anterior/inferior glenohumeral ligament 130 to glenoid/glenoid neck 132 in the shoulder. In this embodiment of the present invention, the time to position the torn ligament is much less and does not require tying sutures over the muscle. As illustrated in FIG. 7, the band of apparatus 134 of the present invention encircles the glenoid neck 132. When cinched, apparatus 134 captures anterior/inferior glenohumeral ligament 130 between the band 134 and the bone.

METHOD

In use, the apparatus of the present invention provides a means for attaching torn or detached tendons and/or ligaments to each other or to underlying bone in order to facilitate the natural healing process. Second end 14 of band 10 is passed through opening 20 so that band 10 encircles both the connective tissue and the tissue or bone to which they are to be attached. The resulting loop is cinched by sliding band 10 in the allowable direction until reaching a closed position. Second end 14 of band 10 is then passed into and through detached clamping head 22. This serves to complete the closed position. Once in this closed position, band 10 securely binds the connective tissue to the desirable tissue or bone.

To adjust and/or remove the apparatus, band 10 can be disengaged by raising end 30 of locking member 26 so that ratchet pawl 28 no longer communicates with plurality of parallel locking grooves 16.

Force can be concentrated or dissipated in a specific area by selecting the placement of bulb element(s) 50 or disk element(s) 72. Force per unit area on the connective tissue can be distributed through the use of wider contact section 90. Where it is desirable to concentrate the force per unit area on the connective tissue, narrower contact section 92 is used. Thus through the selection of contact section width as well as the placement of bulb element(s) 50 and one to a plurality of disk element(s) 72 the surgeon can create the desired connection between the connective tissue and the desirable tissue or bone.

Where the physician desires to attach connective tissue to bone, an alternative apparatus as depicted in FIGS. 6A and 6B can be used. Here, the physician creates a trough or hole in the desired bone, and places bone anchor 110 in this trough or hole. Connective tissue can then be held in place by forming a closed loop around the connective tissue. This is done by passing second end 14 of band 10 through opening 20 thereby encircling the connective tissue and the desireable tissue or bone. The resulting loop is cinched by sliding band 10 in the allowable direction until reaching a closed position. Second end 14 of band 10 is then passed into and through detached clamping head 22. This serves to complete the closed position.

Where the apparatus of the present invention is used to reattach a torn anterior/inferior glenohumeral ligament, from one to a plurality of clamping heads are placed in glenoid neck 132 or other part of the glenoid using bone anchor 110. The band to each corresponding clamping head is then looped around the connective tissue and the desireable tissue or bone and cinched. Appropriate contact section width is preselected. Force is concentrated or dissipated in a specific area by selecting the placement of bulb element(s) 50 or disk element(s) 72. This placement provides for close communication between anterior/inferior glenohumeral ligament 130 and glenoid neck 132, including the anterior glenoid.

Once apparatus 134 has been appropriately positioned, cinched and clamped to form a closed position, the excess band is removed. Excess band is that portion of the band distal to the detached clamping head and not comprising the cinched loop portion of the band. At this point the physician can close the overlying tissue Although the apparatus and method of the present invention has been described in detail for purposes of illustration, it is understood that such detail is solely for that purpose, and variations can be made therein by those skilled in the art without departing from the spirit and scope of the invention. The apparatus and method of the present invention are defined by the following claims.

What is claimed is:

1. A device for attaching connective tissue to each other or underlying bone comprising:

a band; and a detached clamping head;

the band having a top and a bottom with the top having a plurality of parallel locking grooves disposed along the length of the band, wherein the plurality of parallel locking grooves form a locking means when joined with the detached clamping head;

the band having a first and a second end with the first end having an opening that can receive the second end thereby forming a band loop;

the detached clamping head being adapted to receive the band, the detached clamping head having a locking means to engage the band such that when the second end of the band is inserted into the detached clamping head, the movement of the band is restricted to one direction.

2. A device for attaching connective tissue to each other or underlying bone as claimed in claim 1, further comprising:

an enlarged bulb portion on the first end.

3. A device for attaching connective tissue to each other or underlying bone as claimed in claim 1, further comprising:

a bone anchor connected to the detached clamping head.

4. A device for attaching connective tissue to each other or underlying bone as claimed in claim 1, wherein the band is of varying widths.

5. A device for attaching connective tissue to each other or underlying bone as claimed in claim 1, further comprising:

a plurality of disks slidably attached to the band.

6. A device for attaching connective tissue to each other or underlying bone as claimed in claim 1, wherein the device comprises a biocompatable polymer selected from the group consisting of implantable grade nylon, polyethylene, and biosoluble material.

7. A device for attaching connective tissue to each other or underlying bone as claim in claim 1, wherein the parallel locking grooves are formed by multiple asymmetric teeth having peaks and valleys, and wherein the peaks of the multiple asymmetric teeth are no higher that the horizontal plane of the top of the band.

8. A method of attaching torn or detached connective tissue to bone comprising the steps of:

exposing the bone and torn or detached connective tissue;

encircling a band around the bone, wherein the band has a top and a bottom, the top having a plurality of parallel locking grooves disposed along the length of the band, and wherein the band has a first end and a second end;

passing the second end through an opening in the first end of the band to create a loop;

placing the torn or detached connective tissue between the bone and the band in the desired position;

tightening or cinching the band by pulling on the second end of the band to hold the position of the connective tissue and to form a cinched loop;

further passing the second end of the band into a detached clamping head;

sliding the detached clamping head down the band to latch and hold the band in the desired position;

removing a portion of the band distal to the detached clamping head and not comprising the cinched loop; and closing the overlying tissue.

9. A method of attaching torn or detached connective tissue to bone as claimed in claim 8 further comprising:

disengaging the band.

10. A method of attaching torn or detached connective tissue to bone as claimed in claim 9, wherein disengaging the band comprises:

releasing the detached clamping head.

11. A method of attaching torn or detached connective tissue to bone as claimed in claim 10:

wherein the detached clamping head further comprises:
a locked member having at least one ratchet pawl, wherein the rachet pawl engages the plurality of parallel locking grooves disposed along the length of the band; and wherein releasing the detached clamping head comprises:
raising an end of the ratchet pawl, so that it no longer communicates with the multiple asymmetric teeth disposed along the length of the band.

12. A method of attaching torn or detached connective tissue to bone as claimed in claim 8 further comprising:

creating a trough in the underlying bone; and placing a bone anchor in the trough, wherein the bone anchor is attached to the detached clamping head.

13. A method of attaching torn or detached connective tissue to bone as claimed in claim 8 further comprising:

concentrating force in a specific area through placement of one to a plurality of bulb elements and one to a plurality of disk elements, wherein the bulb elements are enlarged sections of the band and the disk elements are slidably connected to the band.

14. A method of attaching torn or detached connective tissue to each other comprising the steps of:

exposing the torn or detached connective tissue;

encircling a band around a first portion of the torn or detached connective tissue, wherein the band has a top and a bottom, the top having a plurality of parallel locking grooves disposed along the length of the band, and wherein the band has a first end and a second end;

passing the second end through an opening in the first end of the band to create a loop;

placing additional portions of torn or detached connective tissue between the first portion of the torn or detached connective tissue and the band, in the desired position;

tightening or cinching the band by pulling on the second end of the band to hold the position of the connective tissue and to form a cinched loop;

further passing the second end of the band into a detached clamping head;

sliding the detached clamping head down the band to latch and hold the band in the desired position;

removing a portion of the band distal to the detached clamping head and not comprising the cinched loop; and closing the overlying tissue.

15. A method of attaching torn or detached connective tissue to each other as claimed in claim 14 further comprising:

disengaging the band.

16. A method of attaching torn or detached connective tissue to each other as claimed in claim 15, wherein disengaging the band comprises:

releasing the detached clamping head.

17. A method of attaching torn or detached connective tissue to each other as claimed in claim 16:

wherein the detached clamping head further comprises:
a locking member having at least one ratchet pawl, wherein the ratchet pawl engages the plurality of parallel locking grooves disposed along the length of the band; and wherein releasing the detached clamping head comprises:
raising an end of the ratchet pawl, so that it no longer communicates with the plurality of parallel locking grooves disposed along the length of the band.

* * * * *